US012564699B1

(12) United States Patent
Yan

(10) Patent No.: US 12,564,699 B1
(45) Date of Patent: Mar. 3, 2026

(54) FUNCTIONALLY MODULAR AROMATHERAPY DIFFUSER

(71) Applicant: Shenzhen Siweiyi Technology Co., Ltd., Shenzhen City (CN)

(72) Inventor: Jing Yan, Ji'an City (CN)

(73) Assignee: Shenzhen Siweiyi Technology Co., Ltd., Shenzhen City (CN)

( * ) Notice: Subject to any disclaimer, the term of this patent is extended or adjusted under 35 U.S.C. 154(b) by 0 days.

(21) Appl. No.: 19/220,655

(22) Filed: May 28, 2025

(30) Foreign Application Priority Data

May 15, 2025 (CN) .......................... 202520962969.0

(51) Int. Cl.
*A61M 21/00* (2006.01)
*A61M 11/02* (2006.01)

(52) U.S. Cl.
CPC ............ *A61M 21/00* (2013.01); *A61M 11/02* (2013.01); *A61M 2021/0016* (2013.01); *A61M 2021/0027* (2013.01); *A61M 2205/07* (2013.01); *A61M 2205/50* (2013.01)

(58) Field of Classification Search
CPC .................. A61M 21/00; A61M 11/02; A61M 2021/0016; A61M 2021/0027; A61M 2205/07; A61M 2205/50
USPC ..................................................... 600/26–28
See application file for complete search history.

(56) References Cited

U.S. PATENT DOCUMENTS 11,197,941 B1 12/2021 Gao
12,350,409 B1 * 7/2025 Jackson .................. A61L 9/122

2009/0105558 A1 * 4/2009 Riley-Doucet ....... A61M 21/00
600/27
2017/0232130 A1 * 8/2017 Conroy ..................... A61L 9/00
422/4
2019/0083671 A1 * 3/2019 McDonnell ........... A61M 21/00
2019/0209805 A1 * 7/2019 Ra Speret ............ A61M 11/005
2020/0289694 A1 * 9/2020 Kelsen .................... A61L 9/122
2021/0261401 A1 * 8/2021 Aiderzada ............ B67D 1/0085
2022/0072182 A1 * 3/2022 Freeman ............... A61M 21/02
2024/0108776 A1 4/2024 Liu (Continued)

FOREIGN PATENT DOCUMENTS

CN 216798341 U 6/2022
CN 219208269 U 6/2023

OTHER PUBLICATIONS

English Translation of CN216798341U (see attached), Jun. 24, 2022, Zheng et al. (Year: 2022).*

*Primary Examiner* — Sunita Reddy

(57) ABSTRACT

A functionally and structurally modular aromatherapy diffuser including: a spraying module provided with an atomizer, wherein one end of the atomizer is connected to an essential oil tube; an essential oil bottle connected to the spraying module, wherein the essential oil tube extends into the essential oil bottle; an accommodating module detachably connected to the spraying module and provided with an accommodating cavity and an air guide assembly, wherein the essential oil bottle is positioned in the accommodating cavity, and one end of the air guide assembly is communicated with the other end of the atomizer relative to the essential oil tube; an air pump module detachably connected to the accommodating module and provided with an air pump; and a main control module detachably connected to the air pump module and provided with a first main control board.

8 Claims, 4 Drawing Sheets

(56)                    References Cited

U.S. PATENT DOCUMENTS

2024/0139366 A1* 5/2024 Chao ........................ A61L 9/013
2024/0335582 A1   10/2024 Ma
2024/0350695 A1* 10/2024 Ma .......................... A61L 9/122

* cited by examiner

FUNCTIONALLY MODULAR AROMATHERAPY DIFFUSER

CROSS-REFERENCE TO RELATED APPLICATIONS

The application claims priority of Chinese patent application CN202520962969.0, filed on May 15, 2025, which is incorporated herein by reference in its entireties.

TECHNICAL FIELD

The present invention relates to the technical field of aromatherapy diffuser, and particularly to a functionally modular aromatherapy diffuser.

BACKGROUND

With the popularity of an aromatherapy diffuser in daily life, a core atomization function of the aromatherapy diffuser has put higher requirements on the durability of an air pump. Currently, the aromatherapy diffuser generates negative pressure by high-frequency driving of an air pump, and atomizes a liquid aromatherapy agent into micron-sized particles. As a core power component, the air pump needs to bear high-load operation for a long time. However, carbon brushes and bearings of a motor inside the air pump are prone to metal fatigue and wear under continuous friction, causing the motor speed to decay or even stop. Meanwhile, an air pump drive circuit is exposed to a high-temperature and high-humidity environment for a long time, and components such as an electrolytic capacitor and a power transistor are prone to thermal aging and oxidation corrosion, causing power supply fluctuations or control signal distortion, and ultimately causing problems such as reduced atomization efficiency and abnormal noise.

In the prior art, the aromatherapy diffuser generally adopts an integrated design of an air pump and a main unit, and an air pump housing is rigidly connected to components such as an atomization chamber and a main control board through welding, bolting or gluing. This structure enables a compact layout but has significant defects: when the air pump fails due to wear or circuit aging, it is difficult for users to disassemble and replace the air pump without damaging a main unit housing or adjacent components, resulting in high maintenance costs and serious waste of resources.

Therefore, there is an urgent need for a modular air pump design solution to lower the maintenance cost and extend the service life of the entire diffuser.

SUMMARY

A primary objective of the present invention is to provide a functionally modular aromatherapy diffuser, which aims to improve the practicality of the aromatherapy diffuser.

To achieve the objective, the functionally modular aromatherapy diffuser provided by the present invention includes:

a spraying module, wherein the spraying module is provided with an atomizer, and one end of the atomizer is connected to an essential oil tube;

an essential oil bottle, wherein the essential oil bottle is connected to the spraying module, and the essential oil tube extends into the essential oil bottle;

an accommodating module, wherein the accommodating module is detachably connected to the spraying module and provided with an accommodating cavity and an air guide assembly, the essential oil bottle is positioned in the accommodating cavity, and one end of the air guide assembly is communicated with the other end of the atomizer relative to the essential oil tube;

an air pump module, wherein the air pump module is detachably connected to the accommodating module, an air pump is provided in the air pump module, and the air pump is communicated with the other end of the air guide assembly relative to the atomizer; and a main control module, wherein the main control module is detachably connected to the air pump module, a first main control board is provided in the main control module, and the first main control board is electrically connected to the air pump.

Optionally, the air pump module includes a mounting housing and a first connecting seat fixed to the mounting housing, the first connecting seat is detachably connected to the accommodating module, and the air pump is fixed in the first connecting seat.

Optionally, the first connecting seat is provided with a first through hole, the air pump includes an air outlet tube protrudingly arranged, and the air outlet tube passes through the first through hole and is communicated with the air guide assembly.

Optionally, the air pump module also includes a second main control board arranged in the mounting housing and a second connecting seat fixed to the other end of the mounting housing relative to the first connecting seat, the air pump is electrically connected to the first main control board by the second main control board, and the second connecting seat is detachably connected to the main control module.

Optionally, a third connecting seat is provided at one end of the accommodating module facing the air pump module, the third connecting seat is detachably connected to the first connecting seat, the third connecting seat is provided with a second through hole, and one end of the air guide assembly is fixed on the second through hole.

Optionally, a fourth connecting seat is provided at one end of the main control module facing the air pump module, and the fourth connecting seat is detachably connected to the second connecting seat.

Optionally, the first connecting seat and the fourth connecting seat are protrudingly provided with a fixed seat, at least one first limiting block and at least one second limiting block are spaced apart from each other on a side wall of the fixed seat, the second connecting seat and the third connecting seat are provided with a limiting groove corresponding to the fixed seat, and an inner wall of the limiting groove is provided with limiting protrusions cooperating with the first limiting block and the second limiting block.

Optionally, a radial dimension of the first limiting block is larger than that of the second limiting block.

Optionally, the main control module includes a control base and a power supply module detachably connected to the control base, the first main control board is arranged in the base and electrically connected to the power supply module, and the power supply module is detachably connected to the air pump module and electrically connected to the air pump relative to the other end of the control base.

Optionally, the functionally modular aromatherapy diffuser further includes a multimedia module, one end of the multimedia module is detachably connected to the main control module and electrically connected to the first main control board, and the other end of the multimedia module is detachably connected to the air pump module and electrically connected to the air pump.

Optionally, the multimedia module is an audio module.

Optionally, the multimedia module is an intelligent voice module.

According to the present invention, the functionally modular aromatherapy diffuser is used to achieve convenient maintenance of the aromatherapy diffuser and includes a spraying module, an essential oil bottle, an accommodating module, an air pump module and a main control module. The spraying module is provided with an atomizer and connected to an essential oil bottle via an essential oil tube, the essential oil tube extends into the bottle to absorb essential oil, and the essential oil is atomized at the atomizer; the accommodating module is detachably connected to the spraying module, an accommodating cavity and an air guide assembly are arranged in the accommodating module, and one end of the air guide assembly is communicated with the atomizer and configured to guide external airflow to the atomizer; the air pump module is detachably connected below the accommodating module, and an air pump in the air pump module is communicated with the other end of the air guide assembly and provides continuous airflow for the atomizer; and the main control module is detachably connected to a top of the air pump module, and a first main control board is provided in the main control module and electrically connected to the air pump to perform electronic control management on the operation of the air pump. According to the modular structure, the functional units may be combined to work together and may also be independently disassembled and maintained. Therefore, when the air pump fails due to motor wear or failure, the air pump can be replaced by detaching the air pump module without disassembling the entire diffuser. This significantly improves the maintainability and service life of the device, thereby improving the practicality and user experience of the aromatherapy diffuser in actual applications.

BRIEF DESCRIPTION OF DRAWINGS

To more clearly illustrate the technical solutions in the embodiments of the present invention or in the prior art, the drawings required to be used in the description of the embodiments or the prior art are briefly introduced below. It is obvious that the drawings in the description below are only some embodiments of the present invention, and those of ordinary skill in the art can obtain other drawings according to structures illustrated in these drawings without creative efforts.

Figure 1:
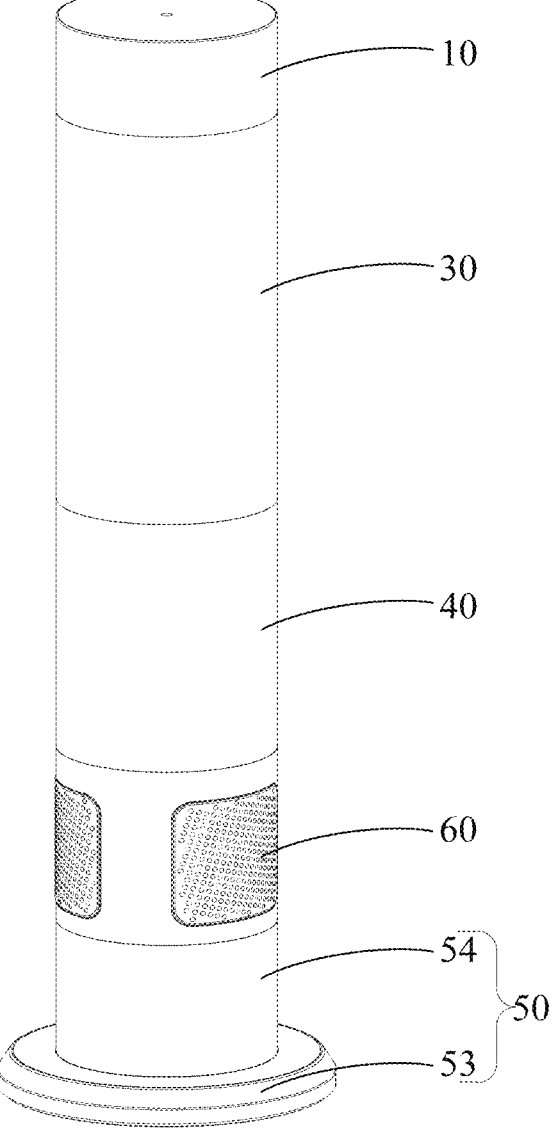
FIG. 1 is a schematic diagram of a structure of a functionally modular aromatherapy diffuser according to the present invention from one angle.

DESCRIPTIONS OF REFERENCE NUMERALS 10. spraying module; 11. atomizer; 12. essential oil tube; 20. essential oil bottle; 30. accommodating module; 31. accommodating cavity; 32. air guide assembly; 33. third connecting seat; 331. second through hole; 40. air pump module; 41. mounting housing; 42. first connecting seat; 421. first through hole; 43. air pump; 431. air outlet tube; 44. second main control board; 45. second connecting seat; 50. main control module; 51. first main control board; 52. fourth connecting seat; 53. control base; 54. power supply module; 60. multimedia module; 70. fixed seat; 71. first limiting block; 72. second limiting block; 80. limiting groove; and 81. limiting protrusion.

The realization of the objectives, the functional features, and the advantages of the present invention will be further explained in conjunction with the embodiments and with reference to the drawings.

DETAILED DESCRIPTION OF EMBODIMENTS

The technical solutions in the embodiments of the present invention will be clearly and completely described below with reference to the drawings in the embodiments of the present invention. It is apparent that the described embodiments are only some, but not all, embodiments of the present invention. Based on the embodiments of the present invention, all other embodiments obtained by those of ordinary skill in the art without creative efforts fall within the protection scope of the present invention.

It should be noted that, if directional indications (such as upper, lower, left, right, front and rear) are involved in the embodiments of the present invention, the directional indications are only used to explain the relative positional relationships, the motion situations and the like between individual components under a certain pose (as shown in the drawings), and if the certain pose is changed, the directional indications are changed accordingly.

In addition, if there are descriptions relating to "first", "second" and the like in the embodiments of the present invention, the descriptions of "first", "second" and the like are for descriptive purposes only and are not to be construed as indicating or implying relative importance thereof or implicitly indicating the quantities of the indicated technical features. Thus, a feature defined by "first" or "second" may explicitly or implicitly include at least one such feature. In addition, "and/or" appearing herein is meant to include three parallel solutions, and taking "A and/or B" as an example, it includes solution A, or solution B, or both solution A and solution B. In addition, the technical solutions among various embodiments may be combined with each other, however, this combination must be based on that it can be realized by those of ordinary skill in the art. When the combination of the technical solutions is contradictory or cannot be realized, such a combination of the technical solutions should not be considered to exist, and is not within the protection scope of the present invention.

The present invention provides a functionally modular aromatherapy diffuser.

Figure 2:
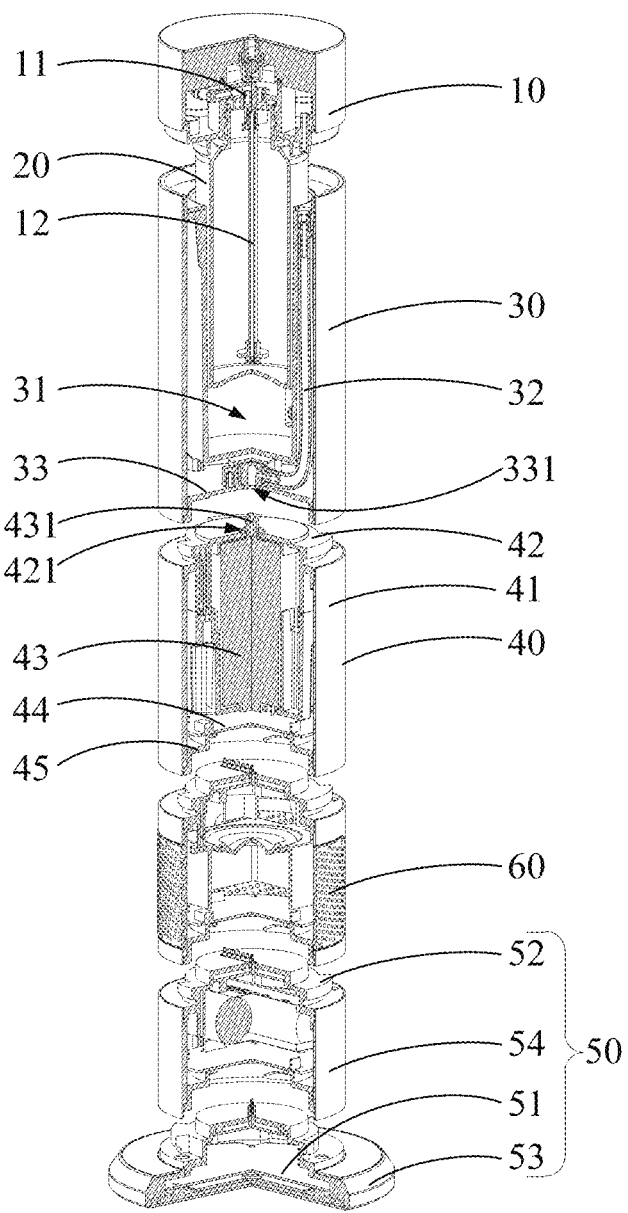
FIG. 2 is a schematic diagram of a partial cross-sectional exploded structure of a functionally modular aromatherapy diffuser according to the present invention from one angle.
Figure 3:
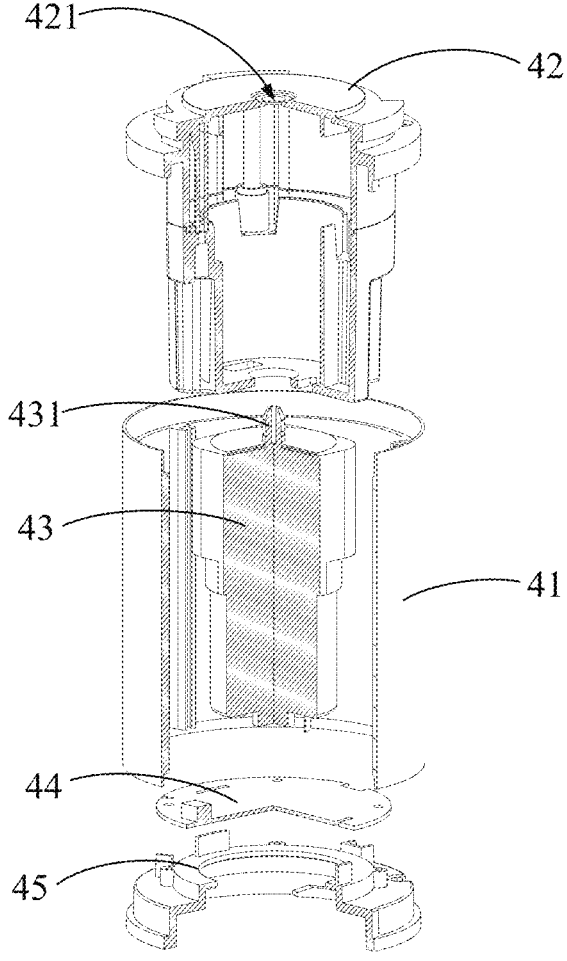
FIG. 3 is a schematic diagram of a partial cross-sectional exploded structure of an air pump module from an angle.
Figure 4:
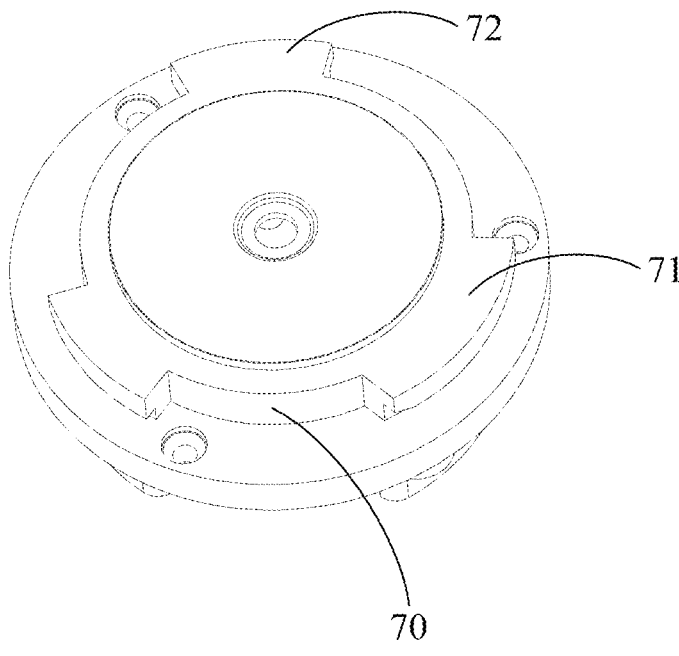
FIG. 4 is a schematic diagram of a structure of a first connecting seat from an angle.
Figure 5:
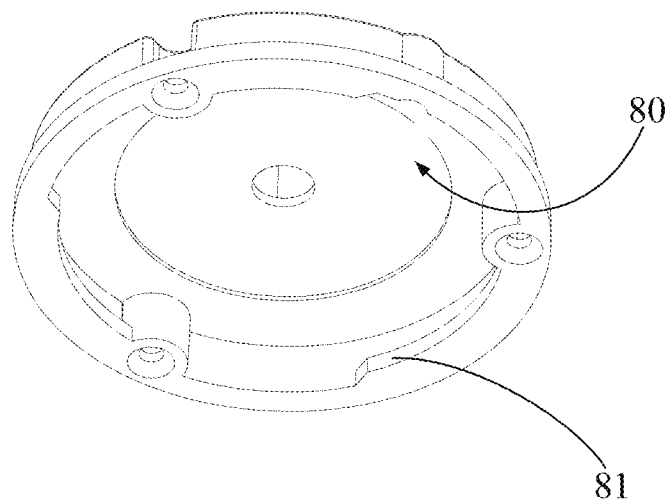
FIG. 5 is a schematic diagram of a structure of a second connecting seat from an angle.

In an embodiment of the present invention, as shown in FIGS. 1 to 3, the functionally modular aromatherapy diffuser includes:

a spraying module 10, wherein the spraying module 10 is provided with an atomizer 11, and one end of the atomizer 11 is connected to an essential oil tube 12;

an essential oil bottle 20, wherein the essential oil bottle 20 is connected to the spraying module 10, and the essential oil tube 12 extends into the essential oil bottle 20;

an accommodating module 30, wherein the accommodating module 30 is detachably connected to the spraying module 10, the accommodating module 30 is provided with an accommodating cavity 31 and an air guide assembly 32, the essential oil bottle 20 is positioned in the accommodating cavity 31, and one end of the air guide assembly 32 is communicated with the other end of the atomizer 11 relative to the essential oil tube 12;

an air pump module 40, wherein the air pump module 40 is detachably connected to the accommodating module 30, an air pump 43 is provided in the air pump module 40, and the air pump 43 is communicated with the other end of the air guide assembly 32 relative to the atomizer 11; and a main control module 50, wherein the main control module 50 is detachably connected to the air pump module 40, a first main control board 51 is provided in the main control module 50, and the first main control board 51 is electrically connected to the air pump 43.

In this embodiment, the spraying module 10 is a core atomizing unit of the aromatherapy diffuser, the atomizer 11 is provided inside the spraying module, the atomizer 11 is connected to a replaceable essential oil bottle 20 via the essential oil tube 12, the essential oil tube 12 is inserted into the essential oil bottle 20 to absorb the stored essential oil, and the essential oil is broken up into fine droplets by a high-speed airflow at the atomizer 11 and is sprayed out from a spraying port at a top of the spraying module 10.

The essential oil bottle 20 is detachably mounted outside the spraying module 10, so that a user replaces essential oils of different scents based on a requirement. A port of the essential oil bottle 20 is calibrated with the spraying module 10, no leakage is ensured through a sealing interface, and the essential oil bottle may be connected by a thread or a snap-fit connection. The specific connection is not limited herein.

The accommodating module 30 is detachably connected to a lower portion of the spraying module 10, an accommodating cavity 31 is provided inside the accommodating module 30 to customize the essential oil bottle 20, and an air guide assembly 32 is arranged to communicate with an outlet of the atomizer 11 for guiding the airflow from the air pump module 40 into the atomizer 11. The detachable structure of the accommodating module 30 makes it unnecessary to disassemble the entire body when cleaning or replacing the essential oil bottle 20.

The air pump module 40 is detachably connected to a bottom of the accommodating module 30, an air pump 43 is mounted inside the accommodating module, and an outlet of the air pump 43 is communicated with the other end of the air guide assembly 32 to provide stable airflow for the atomizer 11. When worn or aged, the air pump module 40 may be removed separately and replaced with a new air pump module 40 without touching the spray or main control parts.

The main control module 50 is detachably mounted on the air pump module 40, a first main control board 51 is assembled inside the main control module, and the first main control board 51 is electrically connected to the air pump 43 to control the starting, the stopping and the air volume of the air pump 43, as well as to manage the atomization mode and the timing function. The independent electrical interface design of the main control module 50 and the air pump module 40 makes it unnecessary to detach the air pump 43 or the spraying unit when the main control board is upgraded or repaired. In addition, the main control module 50 is provided with an electrical connection port for connecting an external power supply to supply power to the air pump 43.

According to the above fully modular design, the aromatherapy diffuser is divided into mutually detachable functional units, so that after the air pump 43 fails due to wear, a user only needs to replace the air pump module 40 alone to restore the normal operation of the aromatherapy diffuser, which greatly improves the maintenance convenience and the sustainable service life of the diffuser.

In addition, according to the above fully modular design, the aromatherapy diffuser may also integrate other functional modules to improve the functional diversity of the aromatherapy diffuser, such as an audio module, an atmosphere light module and a voice module. The specific functional modules are not limited herein.

According to the present invention, the functionally modular aromatherapy diffuser is used to achieve convenient maintenance of the aromatherapy diffuser and includes a spraying module 10, an essential oil bottle 20, an accommodating module 30, an air pump module 40 and a main control module 50. The spraying module 10 is provided with an atomizer 11 and connected to an essential oil bottle 20 via an essential oil tube 12, the essential oil tube 12 extends into the bottle to absorb essential oil, and the essential oil is atomized at the atomizer 11; the accommodating module 30 is detachably connected to the spraying module 10, an accommodating cavity 31 and an air guide assembly 32 are arranged in the accommodating module, and one end of the air guide assembly 32 is communicated with the atomizer 11 and configured to guide external airflow to the atomizer 11; the air pump module 40 is detachably connected below the accommodating module 30, and an air pump 43 in the air pump module is communicated with the other end of the air guide assembly 32 and provides continuous airflow for the atomizer 11; and the main control module 50 is detachably connected to a top of the air pump module 40, and a first main control board 51 is provided in the main control module and electrically connected to the air pump 43 to perform electronic control management on the operation of the air pump 43. According to the modular structure, the functional units may be combined to work together and may also be independently disassembled and maintained. Therefore, when the air pump 43 fails due to motor wear or failure, the air pump 43 can be replaced by detaching the air pump module 40 without disassembling the entire diffuser. This significantly improves the maintainability and service life of the device, thereby improving the practicality and user experience of the aromatherapy diffuser in actual applications.

Further, as shown in FIGS. 1 to 3, the air pump module 40 includes a mounting housing 41 and a first connecting seat 42 fixed to the mounting housing 41, the first connecting seat 42 is detachably connected to the accommodating module 30, and the air pump 43 is fixed in the first connecting seat 42. In this embodiment, the mounting housing 41 serves as a housing structure of the air pump module 40 for providing mechanical support and protection for the air pump 43 and a driving motor of the air pump, and the first connecting seat 42 is mounted inside the mounting housing 41 and serves as a "transfer platform" between the air pump 43 and the accommodating module 30, so as to fix the air pump 43 and also serve as a detachable connection function between the modules. Specifically, the first connecting seat 42 is detachably connected to a bottom interface of the accommodating module 30 by a snap-fitstructure or a threaded structure, and the modular detachment of the aromatherapy diffuser is achieved by a simple connecting structure, which effectively improves the convenience of the aromatherapy diffuser.

Further, as shown in FIGS. 1 to 3, the first connecting seat 42 is provided with a first through hole 421, the air pump includes 43 an air outlet tube 431 protrudingly arranged, and the air outlet tube 431 passes through the first through hole 421 and is communicated with the air guide assembly 32. In this embodiment, the air pump module 40 not only fixes the air pump 43, but also accurately guides the airflow to the air guide assembly 32 in the accommodating module 30. Therefore, a first through hole 421 is formed on the first connecting seat 42, and a protruding air outlet tube 431 of the air pump 43 is used to achieve direct snap-fit. Specifically, the first through hole 421 is positioned at the center of the first connecting seat 42, corresponds to the air outlet of the air pump 43, and is configured to provide a sealed passage for the air outlet tube 431; the air outlet tube 431 is used as an airflow outlet of the air pump 43 and protrudingly provided at an outer side of a housing of the air pump 43; and an end portion of the air outlet tube passes through the first through hole 421 and then is directly connected to the air guide assembly 32, so that the high-pressure airflow generated by the air pump 43 is delivered to the upstream of the atomizer 11 without obstruction.

Further, as shown in FIGS. 1 to 3 the air pump module 40 also includes a second main control board 44 arranged in the mounting housing 41 and a second connecting seat 45 fixed to the other end of the mounting housing 41 relative to the first connecting seat 42, the air pump 43 is electrically connected to the first main control board 51 by the second main control board 44, and the second connecting seat 45 is detachably connected to the main control module 50. In this embodiment, the air pump module 40 not only achieves airflow output, but also integrates local electrical control and electrical interconnection functions between modules. Therefore, the second main control board 44 is added in the mounting housing 41, and the second connecting seat 45 is fixed at one end of the second main control board opposite to the first connecting seat 42. Specifically, the second main control board 44 is mounted inside the mounting housing 41 of the air pump module 40, and is configured to receive a control signal from the main control module 50 for power input, so as to drive the air pump 43 to start or stop, and implement multi-speed air volume adjustment or fault self-detection based on a requirement. The second connecting seat 45 is arranged at one end of the mounting housing 41 opposite to the first connecting seat 42, and is used as a detachable electrical and mechanical connection interface between the air pump module 40 and the main control module 50, so as to ensure reliable transmission of electric energy and signals during modular assembly and facilitate quick assembly and disassembly.

In addition, when the air pump 43 needs to be replaced, the air pump module 40 may be replaced separately, or the first connecting seat 42 and the second connecting seat 45 on the air pump module 40 may be detached, and then the air pump 43 may be removed and replaced separately.

Further, as shown in FIG. 1, a third connecting seat 33 is provided at one end of the accommodating module 30 facing the air pump module 40, the third connecting seat 33 is detachably connected to the first connecting seat 42, the third connecting seat 33 is provided with a second through hole 331, and one end of the air guide assembly 32 is fixed on the second through hole 331. In this embodiment, the accommodating module 30 and the air pump module 40 are quickly connected electrically and mechanically by a dedicated third connecting seat 33, and the sealing and alignment of the air guide assembly 32 is ensured. The third connecting seat 33 is arranged at one end of the accommodating module 30 facing the air pump module 40, and is configured to be in detachable snap-fit with the first connecting seat 42 of the air pump module 40 and achieve the interface conversion and sealing positioning functions between the air guide assembly 32 and an air inlet of the air pump 43. The second through hole 331 is formed on the third connecting seat 33 and corresponds to the first through hole 421, and one end of the air guide assembly 32 is fixed in the second through hole 331 for guiding and conveying the airflow generated by the air pump 43 into the atomizer 11.

Further, as shown in FIGS. 1 to 5, a fourth connecting seat 52 is provided at one end of the main control module 50 facing the air pump module 40, and the fourth connecting seat 52 is detachably connected to the second connecting seat 45. In this embodiment, the main control module 50 and the air pump module 40 are conveniently connected electrically and mechanically by the fourth connecting seat 52 and the second connecting seat 45, so as to ensure reliable transmission of control signals and power supply. Specifically, the fourth connecting seat 52 is arranged at one end of the main control module 50 facing the air pump module 40, and is configured to be detachably connected to the second connecting seat 45 of the air pump module 40, so as to perform dual functions of electrical interface and structural fixation.

Further, as shown in FIGS. 1 to 5, the first connecting seat 42 and the fourth connecting seat 52 are protrudingly provided with a fixed seat 70, at least one first limiting block 71 and at least one second limiting block 72 are spaced apart from each other on a side wall of the fixed seat 70, the second connecting seat 45 and the third connecting seat 33 are provided with a limiting groove 80 corresponding to the fixed seat 70, and an inner wall of the limiting groove 80 is provided with limiting protrusions 81 cooperating with the first limiting block 71 and the second limiting block 72. In this embodiment, to ensure the directional positioning and error-proof locking of the functional modules during "quick-insertion" snap-fit, the first connecting seat 42 and the fourth connecting seat 52 are first configured as fixed seats 70 protruding outward, and the side walls of the connecting seats are sequentially spaced to form at least one set of first limiting blocks 71 and second limiting blocks 72; correspondingly, the second connecting seat 45 and the third connecting seat 33 are provided with corresponding limiting grooves 80 on inner sides of the connecting seats, and limiting protrusions 81 are arranged in pairs on inner walls of the limiting grooves 80 and cooperate with the first limiting blocks 71 and the second limiting blocks 72. The fixed seat 70 is fixedly arranged at outer sides of the first connecting seat 42 and the fourth connecting seat 52, and the first limiting block 71 and the second limiting block 72 are longitudinally arranged at intervals along a side wall of the fixed seat 70 and are configured to bear the limiting blocks and guide the snap-fit when the modules are inserted; the limiting groove 80 and the limiting protrusion 81 are arranged on inner sides of the second connecting seat 45 and the third connecting seat 33, a width and a depth of the limiting groove 80 match a size of the fixed seat 70, and the limiting protrusion 81 is engaged with the corresponding limiting block to achieve locking between the modules.

Further, to further enhance the anti-loosening and anti-error functions of the module insertion, among a pair of limiting blocks arranged on the side wall of the fixed seat 70, a shape and a size (such as a width) of the first limiting block 71 are larger than those of the second limit block 72, thereby avoiding being mistakenly considered to be in place in the reverse or half-inserted state, thereby improving user perception and operational tolerance.

Further, as shown in FIGS. 1 to 5, the main control module 50 includes a control base 53 and a power supply module 54 detachably connected to the control base 53, the first main control board 51 is arranged in the base, the first main control board 51 is electrically connected to the power supply module 54, and the power supply module 54 is detachably connected to the air pump module 40 and electrically connected to the air pump 43 relative to the other end of the control base 53. In this embodiment, the main control module 50 is composed of the control base 53 and the power supply module 54 detachably connected thereto. A first main control board 51 is fixedly arranged in the control base 53 and is responsible for receiving a user instruction and generating control signals for starting, stopping, regulating power and the like of the air pump 43; the power supply module 54 is connected to a bottom of the control base 53 by the limiting of a clamping block, which not only provides a stable working power supply for the main control board, but also reserves a power interface connected to the air pump module 40 at the other end of the main control board, directly outputting the driving current to the air pump module 40. According to the modular design, the user only needs to unplug the power supply module 54 or the air pump module 40 to quickly replace the faulty parts without disassembling the entire device, which effectively improves the practicality of the aromatherapy diffuser.

In addition, the power supply module 54 is further provided with a power connection control board electrically connected to the main control module 50 and a power supply control board for the output circuit.

Further, connecting plates such as a first connecting plate and a third connecting plate are respectively provided at opposite ends of the power supply module 54 to adapt to the module cooperation of the aromatherapy diffuser.

Further, as shown in FIGS. 1 to 5, the functionally modular aromatherapy diffuser further includes a multimedia module 60, one end of the multimedia module 60 is detachably connected to the main control module 50 and electrically connected to the first main control board 51, and the other end of the multimedia module is detachably connected to the air pump module 40 and electrically connected to the air pump 43. In this embodiment, the multimedia module 60 is used to integrate more functional modules into the aromatherapy diffuser. Specifically, one end of the multimedia module 60 is detachably connected to the bottom of the main control module 50, and the built-in circuit board and the functional module in the multimedia module are electrically connected to the first main control board 51 to achieve the multimedia function; and the other end of the multimedia module is detachably connected to the air pump module 40 and achieves power sharing with the air pump module 40, thereby achieving function and power transmission.

In addition, the multimedia module 60 is further provided with a power connection control board electrically connected to the main control module 50 and a power supply control board for the output circuit.

Further, connecting plates such as a first connecting plate and a third connecting plate are respectively provided at opposite ends of the multimedia module 60 to adapt to the module cooperation of the aromatherapy diffuser.

Further, the multimedia module 60 is an audio module, a small speaker and a decoding board are arranged inside the audio module, and the audio module can play a prompt tone or soft background music by sharing an audio signal bus with the main control module 50 through the fourth connecting seat 52, so as to create a better use atmosphere.

In another embodiment, the multimedia module 60 is replaced by an intelligent voice module, a voice recognition and synthesis chip is integrated inside the intelligent voice module, and the intelligent voice module may achieve the voice wakeup, status broadcast and interactive control by connecting to the first main control board 51, so as to further improve the user experience.

The above mentioned contents are only optional embodiments of the present invention and are not intended to limit the patent scope of the present invention, and under the invention concept of the present invention, the equivalent structural transformations made by using the contents of the specification and the drawings of the present invention, or direct/indirect applications to other related technical fields, are all included in the patent protection scope of the present invention.

What is claimed is:

1. A functionally and structurally modular aromatherapy diffuser, comprising: a plurality of coaxially arranged stacked modules including:

a spraying module, wherein the spraying module is provided with an atomizer, and one end of the atomizer is connected to an essential oil tube;

an essential oil bottle, wherein the essential oil bottle is connected to the spraying module, and the essential oil tube extends into the essential oil bottle;

an accommodating module, wherein the accommodating module is detachably connected to the spraying module and provided with an accommodating cavity and an air guide assembly, the essential oil bottle is positioned in the accommodating cavity, and one end of the air guide assembly is communicated with the other end of the atomizer relative to the essential oil tube;

an air pump module, wherein the air pump module is detachably connected to the accommodating module, an air pump is provided in the air pump module, and the air pump is communicated with the other end of the air guide assembly relative to the atomizer; and a main control module comprising a power supply module, wherein the main control module is detachably connected to the air pump module, a first main control board is provided in the main control module and is electrically connected to the power supply module, and the first main control board is electrically connected to the air pump;

wherein each of the modules is configured to be independently and individually disassembled as desired or for maintenance or replacement purpose without requiring disassembling of the entire aromatherapy diffuser;

wherein the air pump module comprises a mounting housing and a first connecting seat fixed to the mounting housing, the first connecting seat is detachably connected to the accommodating module, and the air pump is fixed in the first connecting seat;

wherein the first connecting seat is provided with a first through hole, the air pump comprises an air outlet tube protrudingly arranged, and the air outlet tube passes through the first through hole and is communicated with the air guide assembly;

wherein the air pump module also comprises a second main control board arranged in the mounting housing and a second connecting seat fixed to the other end of the mounting housing relative to the first connecting seat, the air pump is electrically connected to the first main control board by the second main control board, and the second connecting seat is detachably connected to the main control module;

wherein a third connecting seat is provided at one end of the accommodating module facing the air pump module, the third connecting seat is detachably connected to the first connecting seat, the third connecting seat is provided with a second through hole, and one end of the air guide assembly is fixed on the second through hole.

2. The functionally and structurally modular aromatherapy diffuser according to claim 1, wherein a fourth connecting seat is provided at one end of the main control module facing the air pump module, and the fourth connecting seat is detachably connected to the second connecting seat.

3. The functionally and structurally modular aromatherapy diffuser according to claim 2, wherein the first connecting seat and the fourth connecting seat are protrudingly provided with a fixed seat, at least one first limiting block and at least one second limiting block are spaced apart from each other on a side wall of the fixed seat, each of the second connecting seat and the third connecting seat is provided with a limiting groove corresponding to the fixed seat, and an inner wall of each limiting groove is provided with limiting protrusions cooperating with the first limiting block and the second limiting block.

4. The functionally and structurally modular aromatherapy diffuser according to claim 3, wherein a radial dimension of the first limiting block is larger than that of the second limiting block.

5. The functionally and structurally modular aromatherapy diffuser according to claim 1, wherein the main control module comprises a control base and the power supply module is detachably connected to the control base, the first main control board is arranged in the base, and the power supply module is detachably connected to the air pump module and electrically connected to the air pump relative to the other end of the control base.

6. The functionally and structurally modular aromatherapy diffuser according to claim 1, wherein the functionally modular aromatherapy diffuser further comprises a multimedia module, one end of the multimedia module is detachably connected to the main control module and electrically connected to the first main control board, and the other end of the multimedia module is detachably connected to the air pump module and electrically connected to the air pump.

7. The functionally and structurally modular aromatherapy diffuser according to claim 6, wherein the multimedia module is an audio module.

8. The functionally and structurally modular aromatherapy diffuser according to claim 6, wherein the multimedia module is an intelligent voice module.

\* \* \* \* \*